United States Patent [19]
Scholz et al.

[11] Patent Number: 5,584,800
[45] Date of Patent: Dec. 17, 1996

[54] METHOD OF ENCLOSING A BODY MEMBER USING AN APERTURED, EXTRUDED SHEET

[75] Inventors: Matthew T. Scholz, Woodbury; Jason L. Edgar, Bloomington; Dennis G. Welygan, Woodbury, all of Minn.

[73] Assignee: Minnesota Mining and Manufacturing Company, St. Paul, Minn.

[21] Appl. No.: 391,111

[22] Filed: Feb. 21, 1995

Related U.S. Application Data

[63] Continuation of Ser. No. 48,891, Apr. 16, 1993, abandoned.

[51] Int. Cl.$^6$ .................................................. A61F 5/00
[52] U.S. Cl. .................................. 602/6; 602/7; 602/8
[58] Field of Search ................................. 602/1, 2, 3, 6, 602/7, 8

[56] References Cited

U.S. PATENT DOCUMENTS

| | | | |
|---|---|---|---|
| 2,919,467 | 1/1960 | Mercer | 18/12 |
| 3,247,039 | 4/1966 | Schultheiss | 156/167 |
| 3,252,181 | 5/1966 | Hureau | 18/12 |
| 3,300,366 | 1/1967 | Krolik, Jr. | 161/112 |
| 3,630,194 | 12/1971 | Boardman | 128/90 |
| 3,692,023 | 9/1972 | Phillips et al. | 128/90 |
| 3,734,812 | 5/1973 | Yazawa | 161/57 |
| 3,763,858 | 10/1973 | Buese | 128/156 |
| 3,853,124 | 12/1974 | Larson | 128/90 |
| 3,908,644 | 9/1975 | Neinart et al. | 128/90 |
| 3,932,526 | 1/1976 | Koshar | 260/607 A |
| 3,972,323 | 8/1976 | Boricheski | 128/91 R |
| 4,131,114 | 12/1978 | Kirkpatrick et al. | 128/90 |
| 4,143,655 | 3/1979 | Custer et al. | 128/90 |
| 4,152,479 | 5/1979 | Larsen | 428/224 |
| 4,273,115 | 6/1981 | Holland et al. | 602/7 |
| 4,316,457 | 2/1982 | Liegeois | 128/156 |
| 4,351,683 | 9/1982 | Kusilek | 156/167 |
| 4,384,022 | 5/1983 | Fowler | 428/296 |
| 4,411,262 | 10/1983 | von Bonin et al. | 128/90 |
| 4,419,315 | 12/1983 | Kessler | 264/145 |
| 4,441,262 | 4/1984 | Gazzoni | 34/57 D |

(List continued on next page.)

FOREIGN PATENT DOCUMENTS

| | | | |
|---|---|---|---|
| 0110860 | 6/1984 | European Pat. Off. . | |
| 0407056 | 1/1991 | European Pat. Off. . | |
| 0466100A1 | 1/1992 | European Pat. Off. . | |
| 1965998 | 1/1971 | Germany | 264/167 |
| 48-35929 | 10/1973 | Japan | 264/167 |
| 61-108761 | 5/1986 | Japan | 264/177.1 |
| 62-202706 | 9/1987 | Japan | 264/177.12 |
| WO83/02898 | 9/1983 | WIPO . | |
| WO90/14060 | 11/1990 | WIPO . | |
| WO94/03211 | 2/1994 | WIPO . | |

Primary Examiner—Paul B. Prebilic
Attorney, Agent, or Firm—Gary L. Griswold; Walter N. Kirn; F. Andrew Ubel

[57] ABSTRACT

The present invention provides a method of enclosing a body member, comprising the steps of: heating an apertured, extruded sheet comprising a low temperature thermoplastic polymer having a softening or melting temperature less than about 90° C.; wrapping the article about the body member; and molding the wrapped article about the body member such that the article is used as an orthopedic casting material and has a sufficient number of apertures after application to the patient to allow moisture vapors produced by the skin to freely escape through the cast or splint. The present invention also provides a method of enclosing a body member, comprising the steps of: initiating the curing of an apertured, extruded sheet comprising a viscous curable resin having a sufficient yield stress to resist flow at ambient temperature for extended periods of time; wrapping the article about the body member; and molding the wrapped article about the body member such that the article is used as an orthopedic casting material and has a sufficient number of apertures after application to the patient to allow moisture vapors produced by the skin to freely escape through the cast or splint. The apertured, extruded sheet may optionally contain a filler associated with the resin. The incorporation of fillers adds substantially to the strength of the cured casting material as well as to the handling properties of the uncured casting tape or bandage.

17 Claims, 1 Drawing Sheet

U.S. PATENT DOCUMENTS

| | | | |
|---|---|---|---|
| 4,454,873 | 6/1984 | Laufenberg et al. | 128/90 |
| 4,473,671 | 9/1984 | Green | 523/105 |
| 4,502,479 | 3/1985 | Garwood et al. | 128/90 |
| 4,572,171 | 2/1986 | Wegner et al. | 128/90 |
| 4,609,578 | 9/1986 | Reed | 428/76 |
| 4,631,215 | 12/1986 | Welygan et al. | 428/105 |
| 4,634,485 | 1/1987 | Welygan et al. | 156/244.11 |
| 4,667,661 | 5/1987 | Scholz et al. | 128/90 |
| 4,668,563 | 5/1987 | Buese et al. | 428/230 |
| 4,705,840 | 11/1987 | Buckanin | 528/53 |
| 4,841,958 | 6/1989 | Ersfeld et al. | 128/90 |
| 4,899,738 | 2/1990 | Parker | 128/90 |
| 4,912,174 | 3/1990 | Grouiller | 525/415 |
| 5,014,403 | 5/1991 | Buese | 28/170 |
| 5,027,803 | 7/1991 | Scholz et al. | 128/89 R |
| 5,176,621 | 1/1993 | Schulz | 602/8 |
| 5,180,632 | 1/1993 | Edenbaum et al. | 428/252 |
| 5,284,468 | 2/1994 | Nelson | 602/5 |
| 5,382,466 | 1/1995 | Ingham | 428/219 |
| 5,405,312 | 4/1995 | Jacobs | 602/7 |

METHOD OF ENCLOSING A BODY MEMBER USING AN APERTURED, EXTRUDED SHEET

This is a continuation of application Ser. No. 08/048,891, filed Apr. 16, 1993, now abandoned.

FIELD OF THE INVENTION

This invention relates to novel orthopedic casting materials, formed by an extrusion process into an apertured article.

BACKGROUND OF THE INVENTION

Many different orthopedic casting materials have been developed for use in the immobilization of broken or otherwise injured body limbs. Some of the first casting materials developed for this purpose involve the use of plaster of Pads bandages consisting of a mesh fabric (e.g., cotton gauze) with plaster incorporated into the openings and onto the surface of the mesh fabric.

Plaster of Paris casts, however, have a number of attendant disadvantages, including a low strength-to-weight ratio, resulting in a finished cast which is very heavy and bulky. Furthermore, plaster of Pads casts typically disintegrate in water, thus making it necessary to avoid bathing, showering, or other activities involving contact with water. In addition, plaster of Pads casts are not air permeable, and thus do not allow for the circulation of air beneath the cast which greatly facilitates the evaporation and removal of moisture trapped between cast and skin. This often leads to skin maceration, irritation, or infection. Such disadvantages, as well as others, stimulated research in the orthopedic casting art for casting materials having improved properties over plaster of Paris.

A significant advancement in the an was achieved when polyisocyanate prepolymers were found to be useful in formulating a resin for orthopedic casting materials, as disclosed, for example, in U.S. Pat. No. 4,502,479 (Garwood et al.) and U.S. Pat. No. 4,441,262 (Von Bonin et al.). U.S. Pat. No. 4,502,479 sets forth an orthopedic casting material comprising a knit fabric which is made from a high modulus fiber (e.g., fiberglass) impregnated with a polyisocyanate prepolymer resin such as polyurethane. Orthopedic casting materials made in accordance with U.S. Pat. No. 4,502,479 provide significant advancement over the plaster of Paris orthopedic casts, including a higher strength-to-weight ratio and greater air permeability. However, such orthopedic casting materials tend not to permit tactile manipulation or palpation of the fine bone structure beneath the cast to the extent possible when applying a plaster of Paris cast. In this regard, knit fiberglass materials are not as compressible as plaster, and tend to mask the fine structure of the bone as the cast is applied, e.g., the care provider may be limited in "feeling" the bone during reduction of the fracture. Although fiberglass fabrics are somewhat radiolucent they sometimes tend to mask the underlying fine bone structure to x-ray penetration. Oftentimes a fine mesh or a "shadow" can be seen on the x-ray image. This mesh, corresponding to the knitted fiberglass backing, obstructs the penetration of the x-rays and thereby obscures the fine detail of the underlying bone on the x-ray image.

Fiberglass backings have further disadvantages. Most, if not all, commercially available fiberglass casting bandages are comprised of filaments with diameters much larger than 3.5 microns ($\mu$m). While 3.5 $\mu$m fibers are considered by the scientific community to be non-respirable, there exists a sizable number of customers that have become concerned about the inhalation of fiberglass dust generated during cast removal. Moreover, orthopedic casting materials involving knit fabrics such as fiberglass are somewhat expensive, and may be cost prohibitive for some users.

An example of an orthopedic bandage using a polyester fabric which is not a knitted fabric is disclosed in U.S. Pat. No. 3,972,323 (Boricheski). However, the orthopedic bandage disclosed in U.S. Pat. No. 3,972,323 involves the use of plaster of Paris, and thus is subject to the disadvantages outlined hereinabove for plaster of Paris orthopedic casts, including an inferior strength-to-weight ratio and poor air permeability. A second example of an orthopedic bandage using a polyester fabric which is not a knitted fabric is disclosed in U.S. Pat. No. 4,841,958 (Ersfeld et al.). However, the polyester fabric backing disclosed in U.S. Pat. No. 4,841,958 causes the cast to have a somewhat lower strength and a lower rigidity than fiberglass casts. As such, these casting materials require more layers of casting tape to achieve a weight bearing orthopedic cast.

A cast material comprising a filled thermoplastic crystalline solid polyurethane is disclosed in U.S. Pat. No. 4,473,671 (Green). In use, the orthopedic cast material is warmed to a sufficiently high temperature to cause the polymer therein to become soft enough to deform. The orthopedic cast material is molded to conform to the surface shape of the effected portion of the body and then is cooled to room temperature. U.S. Pat. No. 4,454,873 (Laufenberg) discloses an orthopedic cast material comprising a thermoplastic material and a coating of (poly)ethylene oxide. The coating is said to prevent adherence of adjacent convolutions of the cast material when it is molten.

A tubular casting system comprising an integral tubular bulky knitted substrate carrying a hardenable resin and an undercast padding layer is disclosed in International Patent Application No. WO 90/14060 (Blott et at.). A water soluble but resin impervious barrier layer intermediate to the padding and resin bearing layers is discussed.

From the foregoing, it will be appreciated that what is needed in the art is an orthopedic casting material which has both the advantages of plaster of Paris, e.g., good moldability and palpability of the fine bone structure, and the advantages of non-plaster of Paris materials, e.g., good strength-to-weight ratio and good air permeability. In this regard it would be a significant advancement in the art to provide such a combination of advantages without actually using plaster of Paris, thereby avoiding the inherent disadvantages of plaster of Paris outlined herein. It would be a further advancement in the art to provide such non-plaster of Paris orthopedic casting materials which have as good or better properties than the orthopedic casting materials of the prior art, and which can be made to be significantly less expensive, and therefore less cost prohibitive, than prior art orthopedic casting materials employing knitted fabrics such as fiberglass knits. Such orthopedic casting materials and methods for preparing the same are disclosed and claimed herein.

RELATED APPLICATIONS

Of related interest are the following U.S. Patent Applications, filed concurrently with this application and by the assignee of this invention: Novel Casting Materials, Ser. No. 08/049,007, Water Soluble Films Used in Synthetic Casting Tapes, Ser. No. 08/048,234, and Novel Casting Tapes and Resins and Processes Therefor, Ser. No. 08/048,656, which are herein incorporated by reference.

Also of related interest are the following U.S. Patent Applications, filed on Jan. 25, 1993 by the assignee of this invention: Water Curable Resin Compositions—Ser. No. 08/008,743; Orthopedic Support Materials and Method—Ser. No. 08/008678; and Microfiber Fillers for Orthopedic Casting Tapes—Ser. No. 08/008,755 which are herein incorporated by reference for their relevant teachings.

SUMMARY OF THE INVENTION

The present invention provides an article comprising a thermoplastic polymer or a curable-resin extruded apertured sheet useful as, for example, an orthopedic immobilization device. The apertured sheet may optionally contain a filler associated with the resin. Preferred materials comprise a semi-crystalline polycaprolactone polymer and have a sufficient yield stress to resist undesirable flow of the polymer into the article's apertures. The incorporation of fillers into the casting materials of the present invention adds substantially to the strength of the cured casting material as well as to the handling properties of the uncured casting tape or bandage. If desired, articles of the present invention may also comprise fibers or a light-weight scrim to provide increased cohesiveness to the uncured article.

Preferred materials of the present invention possess the moldability and conformability of plaster of Paris casting materials and approach the strength of synthetic fiberglass casting materials. The present invention is useful primarily as an orthopedic immobilization device.

BRIEF DESCRIPTION OF THE DRAWINGS

The invention may be more clearly understood by reference to the drawings, wherein:

In FIG. 1 a fabric structure 1 comprising eight undulated elements 2 contacting and fused to nine parallel elements 3 is depicted. The fabric structure 4 shown in FIG. 2 comprises three helical filamentary structures 5 whose axes are substantially parallel to outer cage filaments 6 and are bonded to these straight, parallel filaments 6. The fabric structure 7 shown in FIGS. 3a and 3b comprise a plurality of filamentary structures 8 randomly fused together. The apertured sheet 9 shown in FIG. 4 is shown with a plurality of apertures 10 drilled or punched through its thickness.

DETAILED DESCRIPTION OF THE INVENTION

The present invention relates to orthopedic casting materials and methods for preparing and using such orthopedic casting materials, wherein the casting materials comprise an apertured sheet formed by extruding a thermoplastic polymer resin or a viscous curable resin. The extrusion process may produce a product with any number of configurations including random forms such as found in Nomad™ matting (available from 3M and described in U.S. Pat. No. 4,351, 683). Alteratively, the apertured sheet may be extruded as a continuous non-apertured film which is then punched or drilled to form an apertured sheet. Presently preferred extruded apertured sheets are formed by the "Z-web" process disclosed in U.S. Pat. Nos. B 14,631,215 and B 14,634, 485 or by the "Spiral" process disclosed in U.S. Pat. No. 4,384,022. Another suitable process, the "Conwed" process, provides an extruded netting having two sets of strands which cross each other at substantially a right angle and which may be molecularly oriented (described, for example, in U.S. Pat. Nos. 2,919,467, 3,252,181, and 4,152,479). The aforementioned patents (U.S. Pat. Nos. 2,919,467, 3,252, 181, 4,152,479, 4,351,683, 4,631,215, 4,634,485, and 4,384, 022) are herein incorporated by reference for their description and teaching of their respective processes.

Figure 1:
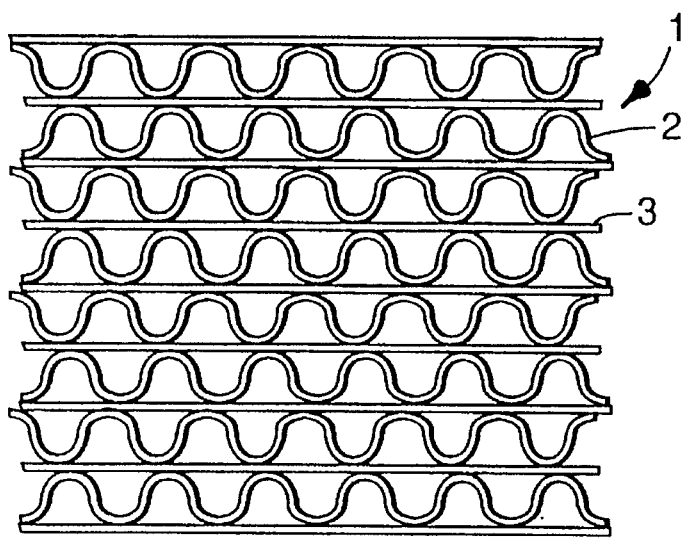
FIG. 1 is a top plan view of a "Z-web" article according to the present invention made employing an extrusion die of the type depicted in FIG. 5 of U.S. Pat. No. 4,631,215 with additional openings of the type shown.

The Z-web process is presently most preferred since it is capable of producing a wide variety of webs having varying density of apertures and thickness and is relatively easy to set up and maintain. The Z-web process works primarily due to differential pressure drops across the die face orifices which results in differential extrudate mass flow rates which create the "zig-zag" or Z-web pattern. A typical web pattern is illustrated in FIG. 1. Articles formed by the Z-web process are manufactured according to the following procedures:

(1) extruding at a first rate (i.e., length of extrudate per unit time) a first filament-forming extrudable plastic mass to form a plurality of straight spaced parallel elements;

(2) extruding (at a second rate faster than the first extension rate and between adjacent spaced, continuous parallel elements) a second filament-forming extrudable plastic mass which is preferably thinner than it is wide to provide a cross-section with an aspect ratio of preferably at least about two, with the undulatable element being positioned with each opposite face of its wide dimension facing one of the straight continuous parallel elements and wherein the plastic masses have a tacky first state which permits the elements to bond to one another at points of mutual contact and a second physical state in which the elements have sufficient structural integrity to maintain their extruded bonded shape and preferably in which latter state subsequent bonding resulting in web deformation and aperture closure will not occur;

(3) while the elements are sufficiently tacky to cause bonding therebetween at points of contact, causing the undulatable element to undulate in its thin dimension by permitting contact between a parallel element on one side of the undulatable element while maintaining the other adjacent parallel element in sufficiently close proximity to permit subsequent contact between it and the undulating undulatable element and to permit repetition of such undulation and subsequent contact, thereby providing an article having an undulated element with apexes aligned on opposed sides wherein the apexes on one side of the undulated element are bonded to one of the parallel elements and the apexes on the other side of the undulated element are bonded to the other adjacent parallel element; and (4) changing or permitting the change of the plastic masses to the second physical state.

Webs made by the Z-web process may aesthetically resemble a knitted web. In order to ensure adequate breathability in a tape form, webs made by the Z-web process preferably have between 7.75 and 77.50 apertures per cm$^2$, more preferably between 15.50 and 62.00 apertures per cm$^2$, and most preferably between 23.25 and 38.75 apertures per cm$^2$. As used herein, a cast which has sufficient porosity to allow moisture vapors produced by the skin to freely escape through the cast is said to be "breathable" or to "breathe." For the Z-web configuration an aperture is defined as a triangular or sinusoidal type aperture as shown in FIG. 1. Preferred Z-web casts are as breathable as typical fiberglass casting tapes such as Scotchcast™ Plus (available from 3M Co., St. Paul, Minn.). Moisture vapor transmission and air flow through a casting material may be tested as described in the examples below. Preferably, the casts of the present invention have comparable air flow and moisture vapor transmission to plaster of Paris materials or traditional fiberglass casting materials.

Figure 2:
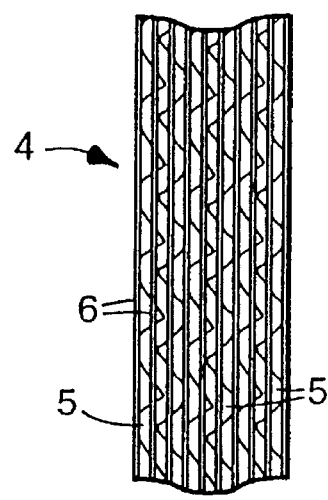
FIG. 2 is a top plan view of a "Spiral" web article according to the present invention made employing an extrusion die of the type depicted in FIG. 9 of U.S. Pat. No. 4,384,022.

The Spiral process is also preferred since it is capable of producing a wide variety of webs having varying density of "apertures" and thickness and is relatively easy to set up and maintain. The Spiral process also works primarily due to differential pressure drops across the die face orifices which results in differential extrudate mass flow rates which create the spiral pattern. A typical spiral web pattern is illustrated in FIG. 2. In contrast to the Z-web process, the Spiral process utilizes a die which comprises one or more inner orifices and a plurality of outer orifices (at least three) which surround each inner orifice. The geometry of the die produces a web which comprises one or more filament bundles having a spiral shaped inner extrudate surrounded by a plurality of straight, parallel outer "cage" filaments. The sizes and cross-sectional shapes of the orifices determine the size and shape of the filaments extruded through them. For a given spacing between the inner orifice and the outer orifices, the pitch of the spiral core filament is determined by the relative material flow through the inner and outer holes. That is, the pitch reduces as the velocity differential increases.

The "Nomad" process is described in U.S. Pat. No. 4,351,683. This process is capable of forming a resilient open fibrous web of inter-engaged continuous kinky filaments. A typical web pattern is illustrated in FIG. 3. The method involves extruding a bundle of filaments of a material having a tacky first state which permits the elements to bond to one another at points of mutual contact and a second physical state in which the elements have sufficient structural integrity to maintain their extruded bonded shape, and in which latter state subsequent bonding will preferably no longer occur, aligning the bundles so the filaments fall upon a contact surface, and advancing the resulting web at a slower rate than the rate of extrusion.

Webs made by the Spiral or "Nomad" processes should have a sufficient number of "apertures" to provide adequate breathability, preferably as much breathability as provided by the Z-web materials. However, due to the geometry of the Spiral webs, and the random nature of the Nomad webs, it is difficult to specifically count the number of apertures per unit area. An alternative method of quantifying the breathability of these webs is to calculate the aperture volume of the web. Suitable webs made by the Spiral or "Nomad" processes have a sufficient percent aperture volume (as defined below) to provide adequate breathability. More preferred webs have as much breathability as provided by the Z-web materials or typical fiberglass casting tapes such as Scotchcast™ Plus from 3M. A web's "aperture volume," as used herein, is determined by first weighing a known volume of web to determine web density. The volume of extrudate in that area of web is then calculated by dividing the measured web weight by the extrudate density. The volume of extrudate divided by the web volume, calculated as the area of the web times its average thickness, gives the fraction extrudate in the mat, which subtracted from one and multiplied by 100 gives the percent aperture volume. The web thickness is determined using an Ames (Waltham, Mass.) model 2 thickness gauge.

In order to ensure good conformability, moldability, and handling, yet provide adequate strength the tape thickness should be between 0.25 and 8.0 mm, more preferably between 0.5 and 4.0 mm, most preferably between 0.75 and 2.00 mm. An orthopedic splint may be formed from multiple layers of thinner tape or may be extruded directly in a thicker form. If extruded directly the material could have from 1.55 to 46.5 apertures per cm$^2$ (or its equivalent aperture volume) and have a thickness of between 2.54 and 12.70 mm, more preferably between 5.08 and 8.89 mm.

Preferred casting tapes of the present invention do not require a scrim component. However, for applications where a higher strength article is desired, the material may comprise a scrim or fibrous material to further enhance the tape's cohesiveness or integrity. Presently more preferably, a fugitive water soluble web is employed as a liner which separates adjacent layers of the tape (e.g., when the tape is provided as a roll). Preferably, the liner is rapidly soluble in water and dissolves when exposed to water in less than about 60 seconds (as described below in the examples), more preferably the liner dissolves when exposed to water in less than 30 seconds and most preferably the liner dissolves when exposed to water in less than 10 seconds. Preferred liners also provide a lubricating effect to the tape when dissolved.

Suitable water soluble liners include polyvinylalcohol ("PVA") and copolymers of PVA, polyacrylamides, polymers incorporating acrylic acid, cellulose ether polymers such as hydroxypropyl cellulose and hydroxyethylcellulose, polyethyloxazoline, polyethylene glycols, polyethylene glycol/polypropylene glycol random and block-copolymers, esters and urethanes of polyethylene glycol or polyethylene glycol and polypropylene oxide polymers and the like. Copolymer films and polymer blends are also possible. Preferably the liner has sufficient flexibility for processing. Some liner materials (e.g., certain PVAs) may require the incorporation of a plasticizer to achieve a suitable degree of flexibility for use as a liner. Suitable plasticizers may be incorporated into the liner either "internally" or "externally" to the polymer. An example of a plasticizer which is "internally" incorporated into the liner is a polymer formed by copolymerizing vinyl acetate with polyethylene glycol monomethacrylate (the plasticizer) followed by hydrolysis to PVA and extrusion as a film. An example of a plasticizer which is "externally" incorporated into the liner is the blending of glycols or other small molecules such as esters into a polymer melt.

Suitable liner films include continuous or non-continuous films. Suitable noncontinuous films include woven or nonwoven films such as melt blown PVA films. Noncontinuous liners may facilitate dissolution of the liner due to their generally high surface area. The presently most preferred liner is Aicello Solublon PVA film SA grade 17 micron thick available from Mitsui Plastics Inc. (White Plains, N.Y.).

In one embodiment of the present invention a casting tape or splint is provided as a thermoplastic apertured web. This embodiment offers an environmentally friendly and hazardfree alternative in casting. For example, casting materials of this embodiment do not require cumbersome disposable liners and will provide a moldable slippery material which is easy to apply. In addition, the product will have very good conformability and should be inexpensive to manufacture.

The basic elements of the thermoplastic casting tape of the present invention include: an extruded apertured web comprising a thermoplastic polymer with controlled amorphous phase rheology, the thermoplastic polymer preferably being softened at less than about 75° C.; an optional water soluble liner; and optional inert or biodegradable fillers. The thermoplastic casting tapes of the present invention may also comprise components containing one or more reactive functional groups suitable for cross-linking the article.

Suitable thermoplastic polymers for use in the present invention are those polymers which soften or melt at temperatures which can comfortably be withstood by the patient and/or technician during the cast's application. This temperature is believed to be less than about 90° C., preferably less than about 75° C., although somewhat higher temperatures may be acceptable (especially in situations where direct contact of the casting material and skin are avoided). Suitable thermoplastic polymers include polyurethanes (especially polyurethanes based on semi-crystalline polyester polyols), polyethylene, ethylene vinyl acetate, cis and trans polyisoprene, polyesters such as polycaprolactone and the like. The currently preferred thermoplastic polymers for use in the present invention are semicrystalline polyesters. Polycaprolactone and blends of polycaprolactone are particularly preferred.

The rheological properties of the thermoplastic material in the amorphous "molten" state are preferably controlled in order to prevent obstruction of the apertures during application (i.e., the "integrity" of the web) and to ensure easy application. This may be accomplished, for example, by incorporating a filler into the polymer, thereby adjusting the blend's rheology (e.g., the blend's yield stress and tan $\delta$ when at application temperature). Alternatively one may blend a polymer having a higher melting temperature, e.g., a polyurethane, into the low melting temperature thermoplastic polymer. Alternatively, one may incorporate unsaturated monomeric or oligomeric species which can be polymerized by heat and/or actinic radiation.

Suitable fillers for use in the present invention are those fillers which are processable in the polymer at the concentrations required to adjust the blend's rheology. For example, a suitable filler is capable of providing the necessary viscosity or yield stress to the polymer blend to prevent obstruction of the apertures during application yet not increase extrusion viscosity to the point where the polymer blend is no longer capable of passing through a die. In addition, the filler morphology and aggregation characteristics should facilitate passage of the filler through the die orifices without causing undesirable plugging or obstruction of the die. Preferred fillers should not prevent bonding of adjacent extrudate streams or cause the web to become unstable. A secondary operation, such as a calendering process, to ensure adequate bonding of adjacent streams may be utilized but is less preferred. Furthermore, preferred fillers should not prevent layer to layer lamination during application and molding.

Suitable fillers for use in the present invention comprise inorganic or organic particulate or fibrous materials which are insoluble in the polymer when the polymer is in the molten or amorphous phase. Filler morphologies may include spheres, bubbles, expandable bubbles, particulate materials, fibers, filaments, microfibers, flakes and platelet type materials, as well as combinations of these. The fillers may have a solid, porous, or hollow structure.

Suitable inorganic filler materials include: glass, amorphous and crystalline silica ($SiO_2$), soda lime borosilicate, amorphous sodium/potassium/aluminum silicate glass, alumina (aluminum oxide), iron oxides, calcium metasilicate, calcium carbonate, calcium sulfate (in either a particulate or microfiber form), kaolin, mica, talc, barium sulfate, boron fibers, carbon fibers, glass fibers, ground glass fibers, flake glass, metallic fibers, feldspar, barium ferrite, titanium oxide, ceramics and the like. Presently preferred inorganic filler materials include glass and ceramic bubbles such as: Scotchlite™ brand glass bubbles H50/10000 EPX, H50/10000 (acid washed), and S60/10000 (available from 3M); Extendosphere brand SG, CG, SF-12 (available from PQ Corp.); Zeeosphere brand 200, 400, 600, 800, and 850 (available from 3M); and Dicaperl brand HP-820, HP-720, HP-520, HP-220, HP-120, HP-900, HP-920, CS-10-400, CS-10-200, CS-10-125, CSM-10-300, and CSM-10-150 (available from Grefco) and ceramic particles such as Ceramcel (available from Microcel Tech. Inc.). Colored pigment fillers are also suitable.

Suitable organic fillers include fillers comprised of thermoplastic or thermoset organic materials or both as well as composite filler materials comprising the following organic materials as matrix and the aforementioned inorganic microinclusions dispersed therein. Suitable organic fillers are insoluble in the molten polymer. Suitable thermoplastic filler materials include those polymers having a relatively high melt temperature (i.e., a higher melt temperature than the low temperature matrix polymer) such as: polyolefins, polyesters (e.g., aliphatic polyesters as well as aromatic polyesters such as poly(ethylene terephthalate), hereinafter referred to as "PET"), polyamides, polyimides, polyacrylates, polycarbonate, polyurethane, styrene-butadiene and the like including copolymers of the aforementioned materials. Suitable thermoplastic filler materials also include materials which are incompatible with the matrix polymer and form phase domains once the matrix polymer cools to room temperature. Suitable thermoplastic filler materials also include expandable bubbles such as Expancel 461 DE 20 microspheres (available from Nobel Industries). Suitable thermoset filler materials include epoxies, aldehyde condensation products (e.g., Ucar Thermoset microballoons BJO-0950, BJO-0820, BJO-0900, BJO-0840, BJO-09300 available from Union Carbide, Danbury Conn.), acrylates, and methacrylates. Preferred organic filler materials include polyethylene microspheres (available from Air Products & Chemicals—Allentown, Pa.).

Preferred particulate fillers have an average particle diameter between 5 and 500 μm, more preferably the particulate fillers have an average particle diameter between 10 and 200 μm, most preferably the particulate fillers have an average particle diameter between 10 and 120 μm. As used herein, "average particle diameter" is defined as the diameter of a sphere of the same volume as the particle.

Microfibers may be added to the resin to enhance web integrity or composite strength. Preferred fibers for use in the present invention have an average length between 25 and 5,000 μm, more preferably the fibers have an average length between 30 and 1,000 μm, most preferably the fibers have an average length between 30 and 500 μm. Microfiber fillers such as those described in U.S. patent application Ser. No. 08/008,751, which is herein incorporated by reference for its disclosure of microfibers, may also be useful alone or in combination with other particulate fillers or fibers.

If desired, the fillers may be surface treated using silanes, titanates, zirconates and the like to enhance bonding, ease of mixing, and compatibility. The surface treatment may be performed prior to incorporation of the filler into the polymer or in-situ, i.e., the surface treatment agent may be incorporated into the suspension for later reaction with the filler.

Preferred fillers also have very low moisture absorbency. Preferably the filler absorbs less than 4% by weight water, more preferably the filler absorbs less than 1% by weight water and most preferably the filler absorbs less than 0.5% by weight water. This is particularly important to facilitate effective extruder processing.

Suitable concentrations of filler in the polymer (i.e., "filler loading") will vary depending on the bulk density of the filler, the specific gravity of the filler, and the particular thermoplastic polymer employed. To account for these variables, it is convenient to measure filler loading in terms of "volume" fraction rather than "weight" fraction. However, the filler's particle size and particle size distribution will also affect filler loading. A suitable filler loading is determined by selecting a level which is sufficiently high to ensure adequate composite strength, acceptable melt viscosity, and good web integrity but not so high that the composite easily fractures or crumbles or is difficult to extrude. A suitable filler loading is determined by selecting a level which is capable of increasing the blend's yield stress to a point where the blend will resist distortions imparted during the application process which cause obstruction of the apertures. Preferably the filler loading is between 1 and 60 volume percent, more preferably the filler loading is between 5 and 40 volume percent, and most preferably the filler loading is between 10 and 30 volume percent.

A second method of controlling the polymer's molten state rheology and thereby increasing web integrity involves the incorporation of a higher melting temperature secondary polymer system. Particularly preferred secondary polymers include those polymers which have strong secondary bonding capability, e.g., hydrogen bonding and ionic interactions, such as polyurethanes, polyvinyl lactams such as polyvinylpyrrolidone, polyamides, ionomers containing carboxylic acid, sulfonic acid, quaternary amine groups, and the like. Preferred secondary polymers have a significantly higher molecular weight or have a significantly higher glass transition temperature than the primary polymer or both. These materials are preferably present at levels of between 5 to 60 percent by weight of the fluid component (i.e., excluding the filler component), more preferably between 10 and 50 percent by weight of the fluid component, and most preferably between 15 and 40 percent by weight of the fluid component.

Alternatively, a material comprising a reactive functional group may be blended into the thermoplastic polymer and reacted in-situ. It is presently believed that the functionalized material would lightly "crosslink," and form an interpenetrating polymer with the thermoplastic polymer, thereby reducing the melt flow of the primary polymer and increase the web integrity. The secondary interpenetrating polymer network may be formed in-situ using a variety of unsaturated vinyl monomers such as monomeric acrylates, methacrylates, acrylamides, methacrylamides, vinyl lactams such as vinyl pyrrolidones, vinyl acetate and its hydrolyzed polymeric derivatives, styrene, olefins, acrylonitriles and combinations of these monomers. Suitable monomers may also be functionalized, e.g., may contain ionic substituents or active hydrogen functionalities such as hydroxyl, primary and secondary amino, mercapto, and carboxyl groups. Polyalkylene oxide substituents are also suitable. The secondary polymer system may be formed exclusively from monofunctional monomeric species or may be formed from compounds having up to to 4 vinyl groups per molecule. Oligomers such as vinyl terminated polyesters and polyurethanes are also suitable. The weight average molecular weight of these oligomers prior to polymerization is preferably between 200 and 100,000, more preferably between 200 and 20,000.

Furthermore, when employing a suitable primary polymer system the secondary polymer system may be formed by a condensation reaction occurring, for example, between a polyfunctional epoxide and a polyactive hydrogen component such as a polyamine or a blocked polyamine such as a kerimine or an imine which regenerates the active amine in the presence of moisture. Alternatively, an isocyanate may be blocked using phenol or another suitable reagent and added in combination with an active hydrogen compound. When heated the isocyanate is regenerated and reacts with the polyactive hydrogen compound to form the secondary polymer system in-situ. Suitable primary resin or polymer systems for these secondary polymer systems include but are not limited to the thermoplastic resins previously disclosed herein and the alkoxy silane functional materials disclosed herein.

Thermoplastic casting materials are applied to the patient after first heating the material above its softening temperature (e.g., in the case of semi-crystalline materials above their melt temperature). Heating of the material may be accomplished in a variety of ways including immersion in hot water, contact with steam, exposure to microwave radiation, contact with dry heat, etc. The use of water or steam is particularly preferred in product constructions which incorporate a water soluble liner and/or hydrophilic resin lubricant. Microwave heating is suitable for materials which absorb microwave energy or employ a microwave susceptor. The warmed casting material is then molded to the desired shape and cooled to harden.

In a second embodiment of the present invention a casting tape or splint is provided as a viscous curable-resin apertured sheet. This embodiment offers a product which will have very good conformability and should be inexpensive to manufacture. Casting materials of this embodiment do not require cumbersome disposable liners or fabric backings and will provide a moldable slippery material which is easy to apply.

The basic elements of the viscous curable-resin casting tape of the present invention include: an extruded apertured web comprising a curable-resin, preferably water curable, having a sufficient viscosity or yield stress to resist flow at ambient temperature for extended periods of time; an optional water soluble liner; and optional inert or biodegradable fillers. The casting tape of the present invention may also comprise a scrim backing.

The viscous curable-resin casting tape of the present invention preferably contains no backing (or only a light weight backing). Therefore, the tape's conformability and handling will be principally determined by the viscosity of the curable resin component. By adjusting the rheological properties of the resin a product with superior conformability and moldability which is also much less expensive to manufacture than current synthetic casting tapes will be possible.

Curing of the resin may be initiated by exposure to water or by a conventional free radical mechanism (e.g., exposing a catalyst to visible and/or ultraviolet light or mixing a two-part catalyst system). Water curable resins are preferred since this is most convenient and familiar to the clinician. Therefore, while the following discussion focuses on water curable resins, it is understood that materials cured by alternative means are suitable.

A significant technical feature of the present invention is the development of a curable resin system, preferably water curable, which can be extruded through an appropriate die and then can be subsequently gelled to a viscous or high yield stress state. The terms "gel" or "gelled," as used herein, describes materials which have or develop a high enough yield stress to resist flow at ambient temperature for extended periods of time. Preferred materials are gelled to a point where the web integrity is sufficient to resist a tension of at least 0.0175 N/mm width, more preferably at least 0.0875 N/mm width and most preferably over 0.175 N/mm width without breaking and without collapse of a substantial portion of the extruded apertures or voids.

Preferred materials have a storage- or elastic- modulus, G', of at least 0.1 dyne/cm$^2$ at 0.1 rad/sec and 1 dyne/cm$^2$ at 1.0 rad/sec. More preferably G' is at least 1 dyne/cm$^2$ at 0.1 rad/sec and 10 dyne/cm$^2$ at 1.0 rad/sec as determined using a parallel plate rheometer such as a Rheometrics Dynamic Analyzer model RDA-II. For ambient temperature curable resins G' is determined at 25° C. under an inert atmosphere. For thermoplastic resins G' is determined at 5 degrees above the melt temperature used in application of the casting material.

A "gelled" resin system may be achieved by forming a composite of the previously mentioned inorganic and organic fillers and the following resin systems. Suitable concentrations of filler in the resin (i.e., "filler loading") will vary depending on the bulk density of the filler, and the specific gravity of the filler and particular resin employed. As used herein, "specific gravity" refers to the ratio of the density of a substance to the density of a reference substance. For solids and liquids the reference substance is water (density=1 g/cc), therefore the specific gravity of a solid or liquid is numerically equal to its density. In contrast, for gases the reference substance is air whose density is 0.00129 g/cc, or 1.29 g/L at 0° C. and 760 mm. For example, the density of hydrogen is 0.089 g/L but its specific gravity is 0.069, (i.e., 0.089/1.29). A suitable filler loading is determined by selecting a level which is sufficiently high to ensure adequate composite strength and good web integrity but not so high that the composite easily fractures or crumbles or is difficult to extrude. Preferably, the filler loading is also high enough to allow the clinician to apply the material to the patient's limb without requiring gloves. Additional methods of controlling the composite's rheology are described below.

The curable-resin used in the casting material of this embodiment of the present invention is preferably any curable resin which will satisfy the functional requirements of an orthopedic cast. Obviously, the resin must be nontoxic in the sense that it does not give off significant amounts of toxic vapors during curing which may be harmful to either the patient or the person applying the cast and also that it does not cause skin irritation either by chemical irritation or the generation of excessive heat during cure. Furthermore, the resin must be sufficiently reactive with the curing agent to insure rapid hardening of the cast once it is applied but not so reactive that it does not allow sufficient working time to apply and shape the cast. Initially, the casting material must be pliable and formable and should adhere to itself. In a short time following completion of cast application, it should become rigid or, at least, semi-rigid, and strong enough to support loads and stresses to which the cast is subjected by the activities of the wearer. Thus, the material must undergo a change of state from a viscoelastic condition (e.g., a material having a high enough yield stress to resist flow at ambient temperature for extended periods of time) to a solid condition in a matter of minutes.

The preferred resins are those cured with water. Presently preferred are urethane resins cured by the reaction of a polyisocyanate and a polyol such as those disclosed in U.S. Pat. No. 4,131,114. A number of classes of water-curable resins known in the art are suitable, including polyurethanes, cyanoacrylate esters, and, when combined with moisture sensitive catalysts, epoxy resins and prepolymers terminated at their ends with trialkoxy- or trihalo-silane groups. For example, U.S. Pat. No. 3,932,526 discloses that 1,1-bis(perfluoromethylsulfonyl)-2-aryl ethylenes cause epoxy resins containing traces of moisture to become polymerized.

Resin systems other that those which are water-curable may be used, although the use of water to activate the hardening of an orthopedic casting tape is most convenient, safe and familiar to orthopedic surgeons and medical casting personnel. Resins such as those disclosed in U.S. Pat. No. 3,908,644 in which a bandage is impregnated with difunctional acrylates or methacrylates, such as the bis-methacrylate ester derived from the condensation of glycidyl methacrylate and bisphenol A (4,4'-isopropylidenediphenol) may be suitable. The resin is hardened upon wetting with solutions of a tertiary amine and an organic peroxide. Also, the water may contain a catalyst. For example, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system). The strength, rigidity and rate of hardening of such a bandage is subjected to the factors disclosed herein.

Some presently more preferred resins for use in the present invention are water-curable, isocyanate-functional prepolymers. Suitable systems of this type are disclosed, for example, in U.S. Pat. No. 4,411,262, and in U.S. Pat. No. 4,502,479. Presently more preferred resin systems are disclosed in U.S. Pat. No. 4,667,661, U.S. patent application Ser. No. 07/376,421 and U.S. patent application Ser. No. 08/048,656, entitled "Novel Casting Tapes and Resins and Processes Therefor" which are herein incorporated by reference. The following disclosure relates primarily to the presently preferred embodiments of the invention wherein water-curable isocyanate-functional prepolymers, water reactive liquid organometallic compounds, or water curable alkoxy silane terminated oligomers are employed as the curable resin.

A water-curable isocyanate-functional prepolymer as used herein means a prepolymer derived from a polyisocyanate compound and a reactive hydrogen compound or oligomer (e.g., a "polyol"). As used herein, a reactive hydrogen compound is a compound having active hydrogen in accordance with the well known Zerevitinov test as described, for example, in Chemistry of Organic Compounds by Carl R. Noller, Chapter 6, pp. 121–122 (1957). The prepolymer has sufficient isocyanate-functionality to cure upon exposure to water, e.g., moisture vapor, or preferably liquid water.

It is presently preferred to employ a polyisocyanate prepolymer formed by the reaction of an isocyanate and a polyol. It is preferred to use an isocyanate which has low volatility such as diphenylmethane diisocyanate (MDI) rather than a more volatile material such as toluene diisocyanate (TDI). Suitable isocyanates include 2,4-toluene diisocyanate, 2,6-toluene diisocyanate, mixture of these isomers, 4,4'-diphenylmethane diisocyanate, 2,4'-diphenylmethane diisocyanate, mixture of these isomers together with possible small quantifies of 2,2'-diphenylmethane diisocyanate (typical of commercially available diphenylmethane diisocyanate), and aromatic polyisocyanates and their mixture such as are derived from phosgenation of the condensation product of aniline and formaldehyde. Typical polyols for use in the prepolymer system include polypropylene ether glycols (available from Arco Chemical under the trade name Arcol™ PPG and from BASF Wyandotte under the trade name Pluracol™), polytetramethylene ether glycols (Polymeg™ from the Quaker Oats Co. and Terathane™ from E.I. Du Pont de Nemours Co.), polycaprolactone diols (Tone™ series of polyols from Union Carbide), and polyester polyols (hydroxyl terminated polyesters obtained from esterification of dicarboxylic acids and diols such as the Rucoflex™ polyols available from Ruco division, Hooker Chemical Co.). By using high molecular weight polyols, the rigidity of the cured resin can be reduced.

The reactivity of the resin once it is exposed to the water curing agent can be controlled by the use of a proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using 4-[2-[1-methyl-2-(4-morpholinyl)ethoxy]ethyl]morpholine ("MEMPE") prepared as described in U.S. Pat. No. 4,705,840, the disclosure of which is incorporated by reference, at a concentration of about 0.05 to about 5 percent by weight (based on total resin weight).

Foaming of the resin should be minimized since it reduces the porosity of the cast and its overall strength. Foaming may occur, for example, when carbon dioxide is released as a result of water reacting with an isocyanate group. One way to minimize foaming is to reduce the concentration of isocyanate groups in the prepolymer. However, to have reactivity, workability, and ultimate strength, an adequate concentration of isocyanate groups is necessary. Although foaming is less at low resin contents, adequate resin content is required for desirable cast characteristics such as strength and resistance to peeling. A satisfactory method of minimizing foaming is to add a foam suppressor such as silicone Antifoam A (Dow Corning), or Anti-foam 1400 silicone fluid (Dow Corning) to the resin. It is especially preferred to use a silicone liquid such as Dow Corning Anti-foam 1400 at a concentration of about 0.05 to 1.0 percent by weight of the resin. Water-curable resins containing a stable dispersion of hydrophobic polymeric particles, such as disclosed in U.S. patent application Ser. No. 07/376,421 and laid open as European Published Patent Application EPO 0 407 056, may also be used to reduce foaming.

In addition lubricants may be added to the resins in accordance with U.S. Pat. No. 4,667,661 such that the casting materials exhibit reduced tack prior to and during cure and yet form a cast with acceptable strength and lamination strength. Suitable lubricants include: hydrophilic groups which are covalently bond to the resin system; additives which are incompatible with the curable resin including: a surfactant, a polymer comprised of a plurality of hydrophilic groups, and a polysiloxane; and combinations of the above. Although U.S. Pat. No. 4,667,661 discusses the addition of lubricants to various curable resins it is presently believed that many of these lubricants would also be useful when added to the thermoplastic polymer compositions of the present invention. The lubricant may be used in conjunction with a separate fugitive liner if desired.

Also included as presently more preferred resins in the instant invention are non-isocyanate resins such as water reactive liquid organometallic compounds. These resins are preferred as an alternative to isocyanate resin systems. Water-curable resin compositions suitable for use in an orthopedic cast consist of a water-reactive liquid organometallic compound and an organic polymer. The organometallic compound reduces resin viscosity and is a compound of the formula $(R^1O)_xMR^2_{(y-x)}$ wherein: each $R^1$ is independently a $C_1$–$C_{100}$ hydrocarbon group, optionally interrupted in the backbone by 1–50 nonperoxide —O—, —S—, —C(O)—, or —N— groups; each $R^2$ is independently selected from the group consisting of hydrogen and a $C_1$–$C_{100}$ hydrocarbon group, optionally interrupted in the backbone by 1–50 nonperoxide —O—, —S—, —C(O)—, or —N— groups; x is an integer between 1 and y, inclusive; y is the valence of M; and M is boron, aluminum, silicon, or titanium. The organic polymer is either an addition polymer or a condensation polymer. Addition polymers are preferably utilized as the organic polymer constituent. Particularly useful addition polymers are those made from ethylenically unsaturated monomers. Commercially available monomers, from which such addition polymers can be formed, include but are not limited to, ethylene, isobutylene, 1-hexene, chlorotrifluoroethylene, vinylidene chloride, butadiene, isoprene, styrene, vinyl napthalene, ethyl acrylate, 2-ethylhexyl acrylate, tetrahydrofurfuryl acrylate, benzyl acrylate, poly(ethylene oxide) monoacrylate, heptafluorobutyl acrylate, acrylic acid, methyl methacrylate, 2-dimethylaminoethyl methacrylate, 3-methacryloxypropyltris(trimethylsiloxy) silane, isobutyl methacrylate, itaconic acid, vinyl acetate, vinyl stearate, N,N-dimethylacrylamide, tert-butyl acrylamide, acrylonitrile, isobutyl vinyl ether, vinyl pyrrolidinone, vinyl azlactone, glycidyl methacrylate, 2-isocyanatoethyl methacrylate, maleic anhydride, vinyl triethoxysilane, vinyl tris(2-methoxyethoxy)silane, and 3-(trimethoxysilyl)propyl methacrylate. Polymers bearing hydrolyzable functionality are preferred. An acidic or basic catalyst may be used to accelerate the water cure of these compositions. Strong acid catalysts are preferred. A more complete description of suitable water reactive liquid organometallic compounds is disclosed in pending U.S. patent application Ser. Nos. 08/008,678 and 08/008,743, which are herein incorporated by reference.

Also included as presently more preferred resins in the instant invention are the water curable alkoxy silane terminated oligomers disclosed in copending U.S. Patent Application "Novel Casting Tapes and Resins and Processes Therefor," Ser. No. 08/048,656. These resin compositions are preferably solventless.

Preferred resin compositions are stable, i.e., nonreactive, and do not significantly increase in viscosity at a temperature of less than about 40° C. In addition, preferred resin compositions are capable of curing upon exposure to water to form a hardened material at a temperature between about 10° to 100° C., preferably at a temperature between about 20° to 50° C. Preferred resin compositions include a low viscosity water-reactive alkoxysilane terminated polymer. The average alkoxysilane functionality is at least one and preferably at least two but may be as high as four. Each alkoxysilane group may have 2 or 3 hydrolyzable groups.

The water-reactive polymer having hydrolyzable terminal alkoxysilane groups is preferably a compound of the formula:

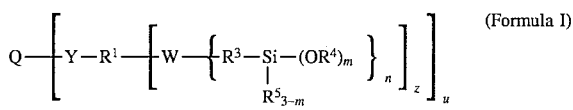

(Formula I)

wherein:
Q is a polyol residue;
W is —NHC(O)—X($R^2_{2-n-q}$)— or —XC(O)NH—;
X= —O—, —N—, or —S—;
Y is —O—, —N—, —S—, carbamylthio (—SC(O)NH—), carbamate (—OC(O)NH) or ureido, and N-substituted ureido (—NHC(O)NH—);
$R^1$ is a substituted or unsubstituted divalent bridging $C_1$-$C_{200}$ hydrocarbon group, optionally interrupted in the backbone by 1 to 50 nonperoxide —O—, —C(O)—, —S—, —$SO_2$—, —$NR^6$—, amide (—C(O)—NH—), ureido (—NH—C(O)—NH—), carbamate (—O—C(O)NH—), carbamylthio (—S—C(O)—NH—), unsubstituted or N-substituted allophanate (—NH—C(O)—N(C(O)—O—)—), unsubstituted and N-substituted biuret (—NH—C(O)—N(C(O)—N—)—), and N-substituted isocyanurate groups;
$R^2$ can be present (if n=1) or absent (if n=2) and is selected from the group consisting of a H and a substituted or unsubstituted $C_1$-$C_{20}$ hydrocarbon group, optionally interrupted in the backbone by 1 to 10 nonperoxide —O—, —C(O)—, —S—, —$SO_2$—, or —N($R^6$)— groups;
$R^3$ is a substituted or unsubstituted divalent bridging $C_1$-$C_{20}$ hydrocarbon group, optionally interrupted in the backbone by 1 to 5 nonperoxide —O—, —C(O)—, —S—, —$SO_2$—, or —N($R^6$)— groups;
$R^4$ is a $C_1$ to $C_6$ hydrocarbon group or —N=C($R^7$)$_2$;
each $R^5$ and $R^7$ is independently a $C_1$ to $C_6$ hydrocarbon group;
$R^6$ is a $C_1$ to $C_6$ hydrocarbon group, or hydrogen;
n=1 to 2 and q=0 to 1, with the proviso that when X is N, n+q=1, and when X is S or O, n+q=2;
u=the functionality of the polyol residue=0 to 6, with the proviso that when u=0, the compound of Formula I is

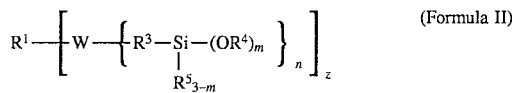

(Formula II)

m=2 to 3; and
z=1 to 3.

Each "$R^3$—Si($OR^4$)$_m$" moiety can be the same or different. A preferred composition consists of toluene diisocyanate ("TDI") based pre-polymers end-capped with highly functionalized alkoxy silanes, such as bis(trimethoxysilylpropyl)amine. The currently preferred prepolymers are those formed from polyols and reactive polyisocyanates with free NCO ranging from 1.9 to 9.0 percent and contain polypropylene glycol, polytetramethylene glycol, and/or polyester ether polyols. The most preferred diisocyanate prepolymers are those containing polyethylene glycol, but include polyether polyols such as polytetramethylene glycol, polypropylene glycols, polybutylene glycols, and random or block copolymers of these, and polymer polyols such as those disclosed in U.S. patent application Ser. No. 07/376,421. Polyolefin polyols such as polybutadiene polyols and polyisoprene polyols may also be used as well as aromatic and aliphatic amine terminated "polyols" such as Jeffamine and Polamine materials, low molecular weight diols, thiols and the like. Mixtures and blends of these polyols may be useful. The preferred average polyol functionality is 1.8 to 3, more preferably 2 to 2.5 but polyols with functionalities as high as 4 or more may be used.

The preferred polyisocyanates have differential reactivity, i.e. have at least one isocyanate group which is significantly more reactive than one or more isocyanate groups on the same molecule by a factor of 2 or more. The preferred isocyanates have a functionality of 2 to 3 while particularly preferred materials have functionalities of 2 to 2.3. The presently preferred isocyanate is TDI. Other aromatic isocyanates such as methylene diisocyanate ("MDI") and polyisocyanates based on condensation products of formaldehyde and aniline are potentially useful. Aliphatic isocyanates are useful and may be particularly preferred for applications where stability to ultraviolet light is of particular concern. Materials such as the trimer and biuret adducts of hexamethylene isocyanate ("HMDI"), methylene-bis-(4-cyclohexylisocyanate), tetramethylxylene isocyanate ("TMXDI"), and xylene isocyanate could be used. Materials such as isophorone diisocyanate and the like are perhaps useful due to the differential reactivity of the isocyanate groups.

The preferred reactive silane of the present invention is bis(trimethoxysilylpropyl)amine, but other reactive silanes could be employed such as aminopropyltrimethoxysilane ("A-1110"), N-beta-(aminoethyl)-gamma-aminopropyltrimethoxysilane ("A-1120"), gamma-mercaptopropyltrimethoxysilane ("Y-11167"), isocyanatopropyl trimethoxysilane, etc. Note that critical elements for a silane useful in the present invention are that it have:

at least one active hydrogen group (except when W=—XC(O)NH—);
at least one silane functionality; and
at least 2 (and preferably 3) hydrolyzable groups in the silane(s).

Preferred silanes are trimethoxy- and triethoxy silanes but other trialkoxy, alkyldialkoxy, aryldialkoxy, and oximino silanes could be useful. These could also be reacted in various combinations and proportions with the TDI-based prepolymers to produce a wide range of average silane functionality (e.g., 2 to 4 or more).

Another important ingredient in the resins is the catalyst for the moisture curable resin. It has been found that substituted guanidines and particularly N,N,N',N'-tetramethylguanidine ("TMG") is the preferred catalyst for these silane cure systems ensuring a sufficiently rapid hydrolysis of the alkoxysilane groups and subsequent condensation of the resulting silanols to form siloxane adducts. However, other basic tertiary amine catalysts could be used in this resin system such as 1,8-diazobicyclo[5,4,0]undecan-7-one ("DBU"), triethylamine, imidazoles, piperazines, etc. Acid catalysts such as sulfonic acids (including alkyl and perfluoroalkyl), carboxylic acids (including alkyl and perfluoroalkyl), phosphoric acids, boric acids and the like could also be employed with this resin system. Moreover, various metal catalysts such as ligands of tin, cobalt, bismuth, lead, zinc or titanium which are known to the an of silane cure could be used alone or in combination with the aforementioned catalysts in this resin system.

Preferably the resin system is highly cohesive to ensure the material will not crack as the product is applied and molded. More preferably, the curable resin compositions have viscosities in excess of 500,000 cps, when measured at 25° C. using a Brookfield RTV Rotovisco viscometer, and have a storage or elastic modulus, G', of at least 0.1 dyne/$cm^2$ at 0.1 rad/sec and 1 dyne/$cm^2$ at 1.0 rad/sec. More preferably G' is at least 1 dyne/$cm^2$ at 0.1 rad/sec and 10 dyne/$cm^2$ at 1.0 rad/sec as determined using a parallel plate rheometer such as a Rheometrics Dyanamic Analyzer model RDA-II. Preferred curable resin compositions have a tan δ less than 20 at 1.0 rad/sec, more preferably a tan δ less than 10 at 1.0 rad/sec, and most preferably a tan δ less than 5 at 1.0 rad/sec. For ambient temperature curable resins, rheological properties are determined at 25° C. under an inert atmosphere.

When formulating the composite materials of the present invention one must strike a balance between the material's uncured "handling" properties (such as web cohesiveness, moldability, etc.) and the material's cured physical properties (such as strength). It is presently believed that the material's physical properties are substantially affected by the composite's filler to resin ratio. As previously mentioned, the addition of filler to a resin can substantially improve the composite's rheology and may even "gel" the composite. Unfortunately, however, as the filler to resin ratio is increased the composite may become less cohesive and more difficult to mold. For a given filler and resin system it may not be possible to formulate a composite which has both high strength and good cohesiveness in the uncured state. To alleviate this problem two different approaches are disclosed in the present invention. The first approach involves a modification to the resin component of the composite. This modification causes a decrease in the resin's tan $\delta$ and thereby increases the composite's cohesiveness. The second approach involves the incorporation of fibers into the composite (either as individual fibers or as a fabric scrim). The fibers provide enhanced cohesiveness to the composite and support some of the tensile forces which are placed on the uncured composite during application. A combination of these methods may be employed if desired.

A material's handling properties may be characterized by measuring the material's rheological properties using a suitable rheometer. A suitable rheometer for evaluating the preferred materials of the present invention include cone and plate or parallel plate rheometers such as the Rheometrics Dynamic Analyzer-II ("RDA-II"), available from Rheometrics Inc. When operated in a dynamic shear mode the rheometer is capable of measuring the elastic modulus (G') and viscous- or loss- modulus (G") of the material. The ratio of G" to G' is referred to as tan delta (tan $\delta$). In general, tan $\delta$ is greater than 1 for a liquid and less than 1 for a solid. When operated in a steady shear mode a parallel plate rheometer is capable of measuring the viscosity ($\eta$) as a function of the applied shear rate ($\gamma$).

As previously mentioned, dramatically decreasing the tan $\delta$ of the resin component is one method of enhancing the composite's (i.e., the resin and filler mixture's) cohesiveness and may be accomplished in a variety of ways. These include: (1) incorporating (i.e., solubilizing) a suitable amount of a high molecular weight secondary polymer into the curable resin; (2) forming an interpenetrating polymer network with the curable resin, e.g., by forming a secondary polymer in-situ through use of a co-cure polymer system; or (3) providing a high concentration of urethane, urea, or other hydrogen bonding functionalities to promote chain interaction; or (4) incorporating prepolymers with a relatively high level of chain branching thereby promoting chain entanglement. Combinations of the above methods may also be employed.

Suitable high molecular weight secondary polymers are those polymers which are soluble in the curable resin and are capable of decreasing the resin's tan $\delta$. Suitable secondary polymers may actually bring the resin to a gel state. Particularly preferred polymers are those polymers which are capable of hydrogen bonding or otherwise interacting with the curable resin system in order to provide adequate viscoelasticity at relatively low addition levels. In general, the amount of secondary polymer added to the resin should modify a suitable rheological property of the resin (and therefore the necessary cohesiveness to the composite) yet not adversely impact the strength and integrity of the cured system. The amount of secondary polymer required to accomplish this function will often depend on the molecular weight of the polymer and the viscosity of the unmodified curable resin or composite. In general, polymer properties are much more dependent on the larger sized molecules in a sample than on the smaller ones. Therefore, the weight-average molecular weight value of a polydisperse sample is a much better indicator of the properties to be expected in a polymer blend than the number average molecular weight and will be used herein unless otherwise noted. When cohesiveness of the casting material is achieved by the incorporation of a high molecular weight polymer, preferred mixtures of polymer and curable resin comprise between 1 and 30% polymer, more preferably between 2 and 20% polymer and most preferably between 2 and 12% polymer. Presently preferred high molecular weight secondary polymers for use in the resin systems of the present invention have a weight average molecular weight ("Mw") between about 30,000 and 5,000,000. More preferably, the high molecular weight secondary polymers have a weight average molecular weight between 100,000 and 3,000,000. Most preferably, the high molecular weight secondary polymers have a weight average molecular weight between 250,000 and 2,000,000.

Polyvinylpyrrolidone ("PVP") has been found to be a particularly useful polymer for decreasing the tan $\delta$ of isocyanate functional polyurethane prepolymer systems. PVP is generally soluble in many polyethylene glycols and polytetramethylene glycols and may be directly added to them as solids and vacuum dried in-situ while heating between about 100° C. and 150° C. Alternatively, resin systems comprising PVP and polyol may be dried azeotropically. Once dissolved in the polyol the resin and polymer solution is preferably formulated under process conditions which prevent the separation of the PVP from the solution. Presently preferred polyurethane prepolymer resin systems comprise between 1 and 12% polyvinylpyrrolidone in the resin (based on the total resin weight and exclusive of any filler). Presently more preferred resin systems comprise between 2 and 10% by weight PVP in the resin. Presently more preferred resin systems comprise between 4 and 8% by weight PVP in the resin. Presently preferred polyvinylpyrrolidone for use in the presently preferred resin systems of the present invention has a weight average molecular weight between about 30,000 and 3,000,000. More preferably, the PVP has a weight average molecular weight between 100,000 and 2,000,000. Most preferably, the PVP has a weight average molecular weight between 250,000 and 1,500,000.

Other suitable polymers for use in the preferred polyurethane prepolymer resin system include acrylate copolymers such as copolymers of isooctyl acrylate and N-vinylpyrrolidone, copolymers of $C_1$–$C_{14}$ acrylates and methacrylates (such as butyl acrylate, butyl methacrylate, isooctyl acrylate, isooctyl methacrylate, acrylic acid, methacrylic acid), acrylamides, methacrylamides and copolymers of butylacrylate and hydroxyethylmethacrylate. Other suitable polymers are those polymers formed from monomers such as N-vinyl lactams such as N-vinylcaprolactone and N-vinyl pyrrolidone, vinyl acetate and its hydrolyzed polymeric derivatives, styrene, olefins, acrylonitrile and the like. Suitable monomers may also be ionic or may contain substituent groups (such as primary and secondary amino, mercapto, hydroxy, and carboxyl groups) which are reactive with the primary resin system. Polyalkylene oxides such as polyethylene oxide, polypropylene oxide, and polybutylene oxide as well as block and random copolymers of these may also be useful as the secondary polymer system. Preferred polymers and copolymers include those based on butyl acrylate, butyl methacrylate, isooctyl acrylate, isooctyl methacrylate, acrylic acid, hydroxyethylmethacrylate, acrylamide, N-vinylpyrrolidone, and polyethylene oxide.

It is understood that the secondary polymer may be polymerized in-situ within the primary resin system, polymerized in a solvent and added to the finished primary resin system, polymerized in a component of the primary resin system such as the polyol or isocyanate, or added to a component of the primary resin system such as the polyol or isocyanate.

An alternative method of providing a highly viscoelastic rosin (thereby facilitating the formation of a cohesive composite) is by forming an interpenetrating polymer network with the curable resin, e.g., by forming a secondary polymer in-situ through use of a co-cure polymer system. One method of accomplishing this goal is by incorporating a second reactive monomer or oligomer system, which is independently reactive, into the primary curable resin. Suitable second reactive monomers or oligomers are preferably independently reactive from the primary curable resin and are capable of forming, in-situ, a high molecular weight secondary polymer. This method offers the potential advantage of allowing processing of the composite material into its final form, or close to its final form, while it still has a relatively low viscosity. The second reactive monomer or oligomer may then be polymerized to form a secondary polymer thereby increasing the viscosity of the resin blend. For example, an unsaturated second monomer or oligomer (such as a mono- or polyfunctional acrylate, methacrylate, acrylamide, or methacrylamide) may be added to an isocyanate functional prepolymer resin system. The second monomer or oligomer may then be polymerized through the use of, for example, heat and/or actinic radiation (visible or ultraviolet light, electron-beam, etc.) to form a polymer therein.

More preferably the second reactive monomer or oligomer may also contain functional groups which will allow the second polymer to later react with the primary cure system. For example, acrylate or methacrylate alcohols are capable of reacting via a free radical mechanism to form a linear polymeric polyol. This polymer is capable of reacting with an isocyanate resin system. Alternatively, an epoxy homopolymerization may be performed through the use of suitable catalysts yielding a polymer containing hydroxyl groups which are capable of further reacting with the isocyanate functional resin.

In systems where the second reactive monomer or oligomer also contains functional groups which will allow the formed second polymer to react with the primary cure system, the ratio of NCO groups to OH groups preferably should be controlled so that sufficient residual reactive isocyanate functionality remains thereby ensuring a rapid and complete cure during application of the device. In addition, the extent of crosslinking of the second reactive monomer or oligomer should be controlled in order to avoid excessive brittleness of the cured composite which may lead to cast breakage by a patient.

A further alternative method of providing a highly viscoelastic resin (thereby facilitating the formation of a cohesive composite) is by providing a composition having a high concentration of urethane, urea, or other hydrogen bending functionality. Suitable additives comprise groups which are capable of promoting hydrogen bonding or polymer chain interaction within the uncured resin system or both. Alternatively, the resin may comprise components with high amounts of chain branching or higher molecular weight oligomers which promote chain entanglements. If desired, both methods may be employed in combination.

In the previously discussed isocyanate functional polyurethane prepolymer systems, the incorporation of higher levels of hydrogen bonding functionality may be accomplished by increasing the number of urethane groups per unit weight of resin and/or incorporating urea groups formed by the reaction of primary or secondary amine functional materials with the isocyanate groups of the resin. The number of urethane groups per unit weight of resin may also be increased through the addition of water to the resin (with a commensurate loss of carbon dioxide). In general, the relative number of urethane groups in the resin will increase as the ratio of isocyanate equivalents to alcohol equivalents (NCO/OH ratio) of a particular resin system is decreased. Furthermore, the relative number of urethane groups in the resin can be increased by using polyols of lower equivalent weights (higher OH numbers).

Additional chain entanglement may also be provided by incorporation of higher molecular weight polyol components and/or by increasing chain branching through the incorporation of polyols and/or isocyanates having a functionality greater than 2. The average functionality can be as high as 6 but is preferably less than 4 and is typically between 2 and 3. Where modification to the functionality of the resin is the primary means of increasing the viscoelasticity of the resin the functionality is preferably between 2.5 and 3.5. A sufficient amount of hard segment (e.g. isocyanate) should be provided to ensure adequate stiffness for rigid immobilization applications. For systems based on Isonate 2143L the concentration of Isonate should be preferably greater than 40% by weight of the resin component (without filler) and more preferably greater that 50% by weight of the resin component (without filler) to ensure the final composite is sufficiently stiff.

As previously mentioned, the process of applying (e.g., wrapping) a cast to a patient's limb imparts a tensile force or stress to the casting bandage or tape. Similarly, the application of a splint to a patient's limb also stresses the splint material. Suitable casting or splint materials should readily survive these application stresses and not break apart during the cast application procedure. Preferred casting tapes of the present invention have a tensile strength greater than about 0.0175 N/mm width, more preferred casting tapes have a tensile strength greater than about 0.0875 N/mm width, and most preferred casting tapes have a tensile strength greater than about 0.175 N/mm width.

Traditional casting products distribute these stresses on the fabric backing or scrim. In contrast, the present invention provides casting materials which preferably have sufficient cohesiveness to resist these application stresses even without a fabric backing or scrim (e.g., by decreasing the resin component's tan $\delta$ through the incorporation of a high molecular weight secondary polymer into the resin, etc.). However, a second alternative method to increase the cohesiveness of the materials of the present invention, i.e. impart higher tensile strength prior to curing and/or increased resistance to cracking during application and curing, is the incorporation of fibers into the composite (either as individual fibers or as a fabric scrim). In this approach, macrofibers are added to the composite to provide enhanced cohesiveness and support some of the tensile forces which are placed on the uncured composite during application. In one embodiment the fibers are added topically (e.g., by a flocking process) as the web comes out of the die. Similarly, a light scrim may be utilized to perform this function. The extruded webs may be bonded to a light weight scrim directly after the extrusion (e.g., the extrudate may be extruded directly onto the scrim) or off-line (e.g., using a secondary process such as a calendering operation). The scrim may also be incorporated between two layers of extruded web to form a three layer laminate. A combination of these approaches is also possible.

Suitable fibers for increasing the cohesiveness of the uncured composite include both inorganic fibers and organic fibers. Preferred inorganic fibers include: fiberglass, and ceramic fibers. Suitable organic fibers include fibers made from: polyester, polyamide (including nylon and Kevlar), polyolefin, polyacrylate, rayon, cotton, hemp, jute, natural rubber, and polyurethane materials. Blends of fibers may also be useful. Suitable fibers have average lengths at least 0.3 cm. Preferred fibers have average lengths between 0.3 and 8 cm, more preferably the fibers are between 1 and 5 cm in length. The fibers may be multifilament or monofilament materials and may comprise filaments between 0.5 and 300 denier. It has been found that incorporation of as little as 1 to 2% by weight of polyester fibers results in a significant improvement in web integrity and cohesiveness. It is presently believed that incorporation of from 1 to 30% by weight of a suitable fiber may be beneficial.

As previously mentioned, it may be also beneficial to incorporate a light conformable scrim into the material—although more preferred articles do not have a scrim component. The scrim may be on the surface of the composite but is preferably embedded in the material. Preferred scrims are light-weight and generally comprise less than 10% by weight of the composition. The scrims are preferably porous to allow the composite to pass moisture vapor and air. Preferred scrims are thin with fairly large openings in order to allow bonding of the material on either side of the embedded scrim. Suitable scrims include knits, wovens, non-wovens and extruded porous sheets. Suitable scrims are also preferably extensible and are comprised of fiberglass, ceramic fibers, polyester, polyolefin, polyamide, polyurethane, natural rubber, cotton, rayon, hemp, jute and the like.

If desired a heavier scrim such as a traditional fiberglass knit may be utilized in the casting products of the present invention. While this is not preferred, for the reasons previously mentioned, fiberglass knits provide sufficient support and porosity. Suitable scrims for use in the present invention are disclosed in pending U.S. patent application No. 08/008,751, which is herein incorporated by reference. Where fiberglass backings are desired, suitable sheets which may be employed are knit fiberglass fabrics such as disclosed in U.S. Pat. Nos. 4,502,479; 4,609,578; 4,668,563; and 5,014,403 and in U.S. patent application Ser. No. 07/976,402. Particularly preferred sheets of this type are extensible, heat-set fabrics as disclosed in U.S. Pat. No. 4,609,578 (Reed) which is herein incorporated by reference for its disclosure of suitable scrims.

The present invention also provides casting materials containing resins which possess a "creamy" movable feel during application. It has been found that the initial water absorbency of a resin system can be controlled by the proper selection of polyol and isocyanate and, if present, the secondary polymer. For example, these components can be blended to provide a resin which is sufficiently hydrophilic to allow the resin to become creamy and feel "movable" or actually allow movement of the resin much like plaster of Paris. This facilitates a smooth finish to the cast and greatly enhances cast moldability.

Incorporation of suitable amounts of polyethylene glycol into the resin formulation provides a creamy "movable" resin. Yet even when the resin becomes movable no mess is created if the filler level of the composite is maintained high enough and the resin is sufficiently viscous. Nevertheless, as the resin becomes even more movable it may be necessary for the clinician to wear gloves to avoid transfer to the hands. Preferred composite systems incorporate a sufficient amount of hydrophilic components to provide a movable resin. As used herein "movable" or "movable resin" refers to a resin which after activation with water but before setting becomes creamy on the surface and can be physically redistributed by hand to smooth the surface of the molded cast in a manner similar to a plaster of Paris cast.

Resin systems may also be colored for decorative purposes using dyes or pigments or both. Luminescent pigments may also be employed. Furthermore, one may alternatively wrap the splint or cast of the present invention with a decorative or informative sheet comprising raised lettering and/or figures which is capable of leaving impressions in the material. One may also provide multicolored printed decorations by, for example, ink jet printing, transfer printing, and pigment printing methods.

The materials and compositions of the present invention may be fabricated into a variety of configurations including splints, tapes, and preformed shapes such as tubes. When fabricated as a splint, the material may be provided as a precut slab or a continuous length form with or without a covering and/or padding. Suitable coverings and paddings for use in this invention are discussed in U.S. Pat. Nos. 5,027,803 and 4,899,738 which are herein incorporated by reference for their disclosure of such coverings and paddings. The splint may have a padding material on one or both sides. The materials and compositions of the present invention may also be supplied as a prepadded unitary splint in tubular form such as that illustrated in FIG. 6 of U.S. Pat. No. 5,027,803.

The following examples are offered to aid in understanding of the present invention and are not to be construed as limiting the scope thereof. Unless otherwise indicated, all parts and percentages are by weight.

EXAMPLES

Example 1

Thermoplastic Apertured Casting Article

Using a Haake Rheomex/Transfermex S-30 extruder (available from Haake Inc., Saddlebrook, N.J.) a 10 kg batch of Tone-767 polycaprolactone, believed to have a number average molecular weight about 30,000 (available from Union Carbide Corp., Danbury, Conn.) was extruded through a die to form a "Z-web" article. The die's openings are as depicted in FIG. 23 of U.S. Pat. No. 4,631,215. The die had 24 slots (measuring 1.12 mm high by 0.36 mm wide) and 25 pairs of circular holes (having 0.43 mm diameters and being vertically separated by 0.56 mm as measured from center-to-center). The distance between the center lines of a pair of holes and a slot was 1.59 min. The extruder was purged with about 2 kg of 4310 grade Elvax (available from E.I. Dupont de Nemours Co., Wilmington, Del.) prior to extrusion of the Tone-767.

A 17 micron polyvinyl alcohol film (available as PVA film SA grade Aicello Solublon from Mitsui Plastics Inc., White Plains, N.Y.) was unwound under the die so that the Tone-767 extrudate flowed at a width of about 2.54 cm directly onto it. Initially no external devices were used to cool the web which made collection of the web difficult without distortion of the shape of the web. Chilled rollers or a water cooled belt could possibly be used to cool the web and avoid this difficulty, nevertheless the PVA unwind operation was discontinued and the web was vertically passed through a quench tank filled with 15° C. water and equipped with a vertically stacked double nip roll assembly. The extruded web had a thickness of 0.178 cm and had about 30.8 pores per cm². In a second operation a length of PVA film was laminated to the extruded web, once it had dried, as described in Example 5.

A 20.3 cm long strip of the web/film laminate was heated in a water bath at 68° C., then molded around a finger. The film dissolved rapidly and the layers of tape adhered well to each other resulting in a breathable casting article. The strength of the article was sufficient to immobilize and support the fingers.

The extruder apparatus and its operating conditions were as follows: screw diameter —3.0 cm; screw length—90 cm; die width—5.1 cm; zone 1 temperature—55° C.; zone 2 temperature—80° C.; zone 3 temperature—105° C.; zone 4 temperature—105° C.; zone 5 temperature—105° C.; zone 6 temperature—105° C.; die temperature—113° C.; pressure at the die—695.6 kg/cm2; screw rotation speed—14 rpm.

Example 2

Z-web Article

A 1 kg batch of Tone-787 polycaprolactone believed to have a number average molecular weight 80,000 (available from Union Carbide) was extruded at 74 rpm using a Haake Rheomex 90 extruder equipped with a Rheomex 90 computerized control panel with specifications and conditions described below. The polycaprolactone was extruded downwardly into a quench tank filled with cold water (50° C.). As the polymer exited the quench tank it was wound on a 7.6 cm cardboard core using a pneumatic motor. The Z-web thusly obtained flowed smoothly and the individual "Z" filaments adhered well to the adjacent straight filaments.

The extruder apparatus and its operating conditions were as follows: screw diameter —2.54 cm; screw length—45.7 cm; zone 1 temperature—150° C.; zone 2 temperature—180° C.; zone 3 temperature—190° C.; zone 4 temperature—200° C.; zone 5 temperature—200° C.; screw rotation speed—74 rpm.

Example 3

A 9.07 kg batch of Tone-767 polycaprolactone was milled with 8–10 micron average particle size calcium carbonate by feeding the calcium carbonate at 2.27 kg/hour and the polycaprolactone at 6.8 kg/hour through a twin screw extruder at 66° C. and into a cold water bath. The mixture was then pelletized by passing the extrudate through a knife-wheel to yield pellets 0.343 cm in length and 0.318 cm in diameter.

The filled polymer was then extruded to form a Z-web using the extruder described in Example 6 and under the following conditions: zone 1 temperature—50° C.; zone 2 temperature—85° C.; zone 3 temperature—95° C.; zone 4 temperature—95° C.; zone 5 temperature—95° C.

The extrudate flowed smoothly and the Z-web had improved integrity compared to the Tone-767 extrudate of Example 1.

Example 4

A 4.54 kg batch of Estane 58312 polyurethane (available from BF Goodrich Co., Cleveland, Ohio) was milled with 4.54 kg of Tone-767 polycaprolactone using a twin screw extruder. All zone temperatures were set at 149° C. and the mass flow rates were 4.54 kg/hour. After cooling in a water bath the blend was pelletized as described in Example 3.

Based on observation of the blend's rheological and physical properties it is believed that this blend is suitable for extrusion into a casting tape article and will provide suitable melt viscosities in the molten state. Blends having lower concentrations of the Estane polyurethane are also believed to be suitable.

Example 5

A 2.54 cm×15.24 cm sample of polycaprolactone extruded in a Z-web form as described in Example 1 (but without a PVA liner) was placed on the bottom unheated plate of a Dake Model 44-027 hydraulic press (available from Dake Corp., Grand Haven, Mich. and equipped with two heatable plates 23 cm×30.5 cm). On top of the Z-web sample was placed a piece of PVA liner so that the entire piece of Z-web was covered with PVA (Aicello Solublon grade SA). A metal plate was placed on top of the web and liner. The upper plate of the hydraulic press was heated to 90° C. and lowered until the hot plate just touched the metal plate on top of the PVA film. The press was left in this position for several seconds and then was opened. The PVA liner adhered to the Z-web and was strongly bonded after cooling.

This demonstrates that the liner can be adhered to the Z-web in a secondary operation.

Example 6

A luminescent pigment (ZnS) (available from USR Optinox Inc., Hackettstown, N.J., as Pigment 2330) fed at 0.36 kg/hr was milled into Tone-767 polycaprolactone fed at 6.8 kg/hour to give a pigment concentration of approximately 5% by weight. An ATV Model MT2030TC twin screw extruder (available from ATC Chemical Machinery Inc., Sagena, Mich. and having its barrel temperatures set at 65° C.) was used to blend the materials. After exposure to natural or artificial light the blend in the dark is intensely illuminated. This blend can be extruded to give a colored luminescent Z-web.

Example 7

A 30.48 cm length of 2.54 cm wide Z-web (consisting of Tone-787 polycaprolactone which had been extruded in Z-web form using the machine and conditions described in Example 1) was placed under a 33.02 cm long strip of 7.62 cm wide 17 micron thick PVA liner (Aicello Solublon grade SA). The two layers were fed under the top roller of a 7.6 cm wide Model XRL 120 laminator (available from Western Magnum Corp., Seguno, Calif.). The temperature of the top roller was set at 90° C. and the temperature of the bottom roller was left unheated (23° C.). After passing through the laminator (speed setting #"2", pressure setting #"0") an excellent bond between the layers was obtained. A second run changing only the speed (to setting #"5") also produced an excellent well bonded laminate.

Example 8

Rate of Dissolution of Various Water-Soluble Films

The time required to "dissolve" a water soluble film is characterized in accordance with the following test method. A single layer of film is cut and secured between the top and bottom halves of a Millipore Filter Holder (Part #4 but without its standard filter screen—Millipore Corp., Bedford, Mass.) to provide a 3.5 cm diameter piece of film secured in place. Twenty milliliters of water is gently added to the top of the fixture (creating approximately a 2 cm head atop the film) by pouring the water down the side of the fixture. The time for the water to dissolve the film and "break-through" the film (i.e., flow through the film) is recorded. Dissolution time is recorded as the mean break-through time of ten samples and is reported below in Table 8a.

TABLE 8a

| Run | Film | Thickness (micron) | Dissolution time (sec.) Undried film | Dissolution time (sec.) Dried film[4] |
|---|---|---|---|---|
| 1 | QSA 2004[1] | 38 | 12.5 | 24.9 |
| 2 | QSA 2004 | 51 | 23.5 | 50.3 |
| 3 | QSA 2000[1] | 38 | 21.3 | 47.2 |
| 4 | QSA 2000 | 51 | 37.0 | 96.1 |
| 5 | Aicello Solublon SA[2] | 17 | 2.7 | 3.7 |
| 6 | EM1100[3] | 53 | 22.3 | 49.9 |

[1]Available from Glenn Corp., St. Paul, Minn.
[2]Available from Mitsui Plastics Inc., White Plains, NY.
[3]Hydroxypropylmethylcellulose (CAS No. 009004-65-3) available from Glenn Corp., St. Paul, Minn.
[4]Dried for 20–24 hours at 100° C.

The above test yields a good approximation of the time required for dissolution of a film. However, as an alternative embodiment of the present invention one may choose to forego use of a separate film of liner and instead directly laminate the casting material with a water-soluble liner material. This liner film may be difficult, if not impossible, to later separate from the casting material and test in accordance with the above method. To test these liner materials it is acceptable to either employ a functional test (i.e., directly measure the casting tape under conditions of use and measure the time required for the liner to provide a lubricating effect) or a modification of the above "break-through" test. For example, one may directly form the liner film against the bottom surface of the Millipore filter (with the same thickness as found on the casting material) and then conduct the breakthrough test. Alternatively, one may form the liner film against the bottom surface of any other suitable porous substrate and place the laminate in the Millipore apparatus for testing as described above.

Example 9

Moisture Vapor Transmission Through a Casting Material

The moisture vapor transmission of various casting materials may be measured using the following test. A ring of casting material measuring between 5 and 10 cm high and having a 5.08 cm inner diameter is formed by curing the material against a stockinet covered mandrel. Alternatively, the ring may be formed by gluing together two fully cured half rings (i.e., "C" shaped sheets having an inner radius of 2.54 cm) using a water impermeable sealant. Prior to testing, the casting material is allowed to cure for 24 hours. The surface area of the cylinder (A) is taken as the inner circumferential area, less any areas (such as seam areas) which were occluded with sealant. The average thickness of the cast material is also recorded (T). For comparison purposes the average thickness of the casting material being tested should preferably be that thickness which provides a comparable ring strength (as described in column 15 of U.S. Pat. No. 4,705,840) to 6 layers of 3M Scotchcast™ Plus casting tape, i.e., approximately 90 N/cm width (±45 N/cm width).

The cylinder of cast material is then sealed completely around its lower circumference to a lower petri dish using a silicone sealant such as Silastic RTV silicone sealant No. 732 (available from Dow Corning Co., Midland, Mich.). The sealant is allowed to cure for 24 hours. A 25 ml beaker of deionized water is placed inside the cylinder and on top of the lower petri dish. Care is taken to not spill the water from the beaker. The top of the cylinder is then closed by sealing a second petri dish on the top circumference using the aforementioned RTV sealant. The sealant is allowed to cure for 12 hours.

The total weight of cast material, petri dishes, beaker, and water is recorded. The samples are then placed in a 37.8° C. oven having a relative humidity of between 24 and 30 percent. The samples are removed periodically and weighed. The weight loss per unit time is calculated as the slope of the weight loss vs. time plot. The slope may be calculated using a least squares line fitting method if desired. The results are expressed as the slope of the weight loss vs. time divided by the area, A, of the cast material. The "moisture vapor transmission" is expressed in units of g water lost/day/sq cm.

A traditional plaster of Paris material and a traditional synthetic fiberglass material were tested for moisture vapor permeability. The plaster of Paris material was Synthetic Plus™ Plaster (cat. no. 4900-03 available from Depuy Co., Warsaw, Ind.). The fiberglass material was Scotchcast™ Plus (available from 3M Co., St. Paul, Minn.). For the fiberglass and Plaster samples two replicates were run.

TABLE 9a

| Run | Sample | Vapor transmission (g water lost/day/sq cm) |
|---|---|---|
| 1 | Scotchcast Plus (6 layers) | 0.413 |
| 2 | Plaster: Synthetic Plus ™ Plaster (Depuy)(15 layers) | 0.185 |

An extruded article produced by the processes of the present invention and having at least 20 percent aperture volume should exhibit similar vapor transmission rates to the Scotchcast™ control. Preferred apertured webs of the present invention have a moisture vapor transmission rate of at least 0.1 g water lost/day/sq cm, more preferably at least 0.2 g water lost/day/sq cm, and most preferably at least 0.4 g water lost/day/sq cm.

Example 10

Air Flow Through a Casting Tape

One advantage of the webs of the present invention is their relatively high aperture volume which allows the cast to "breathe" during wear. The breathability of a several traditional casting tapes was characterized according to the following test. For comparison purposes the average thickness of the casting material being tested should preferably be that thickness which provides a comparable ring strength (as described in column 15 of U.S. Pat. No. 4,705,840) to 6 layers of 3M Scotchcast™ Plus casting tape, i.e., approximately 90 N/cm width (±45 N/cm width).

A W. & L. E. Gurley Densometer Model 4110 (Troy, N.Y.) attached to a Gurley-teledyne sensitivity meter (Cat. No. 4134/4135—used for calibration) and an Engler Instruments Co. Model 605 timer was used to measure the flow of air through the web specimen. Specifically, this instrument measured the time in seconds required to pass 10–50 cc of air through a 6.45 square cm piece of 0.64 cm thick cured casting tape. The test was performed in a room having a temperature between 23° and 25° C. and about 50% relative humidity.

The samples were prepared in the following manner. In the center of both sides of a 5 cm×5 cm square piece of cured web was adhered a 2.54 cm diameter circular piece of Microfoam tape (3M Company, St. Paul, Minn.). Next, the entire sample (top, bottom, and sides) was sealed using Dow Coming 732 RTV multipurpose silicone sealant (Midland, Mich.). The samples with sealant were allowed to cure overnight. Once cured the microfoam tape circles were gently removed using a tweezers to leave a 2.54 cm diameter circular opening through which air could be passed.

The top surface was then covered with a piece of Scotch Brand #471 yellow plastic tape (available from 3M Co., St. Paul, Minn.) which had a mating 2.54 cm diameter hole. Initially the bottom surface was covered with a piece of Scotch Brand #471 yellow plastic tape (without a hole therein).

The sample was then tested for its leak rate, i.e., the rate at which air leaked through imperfections in the seal and/or sealant layer. The leak rate ("L" in cc/sec) of the sample was determined by placing the sample in the Densometer and measuring the air flow, i.e., the time required to pass a known volume (e.g., 10 to 50 cc) of air. Next the lower occluded layer of tape was replaced with a layer of tape identical to that on the top of the sample except that a 2.54 cm diameter hole was cut and aligned with the sample hole. The air flow rate through the sample and sealant was measured as previously described ("F" in cc/sec). By subtraction the air flow through the sample was then determined by the following formula: actual sample air flow=F–L (cc/sec). The following air flow results were found:

TABLE 10

| Run # | Material | Flow (cc/sec) |
| --- | --- | --- |
| 1 | OCL Plaster Splint (15 layers) | 0.04 |
| 2 | 3M Scotchcast ™ Plus (6 layers) | 1028 |

For materials with a high air flow value it may be necessary to either increase the volume of air passed, e.g., 300 cc, or decrease the surface area which is open to air flow. However, if the circular opening is reduced the air flow value must be corrected, i.e., normalized to an equivalent air flow per unit area, prior to comparing samples. For example, if a sample was prepared with a 1.27 cm circular hole in place of the 2.54 cm circular hole described above the air flow obtained would be multiplied by 4 to yield a proper comparison.

Extruded articles, having a thickness which provides a comparable strength to Scotchcast™ Plus as described above, produced by the processes of the present invention and having at least 20 percent aperture volume should exhibit similar air flow rates to the Scotchcast™ control.

Preferred apertured webs of the present invention have an air flow rate of at least 50 cc/sec, more preferably at least 100 cc/sec, and most preferably at least 400 cc/sec.

Example 11

Casting Article Produced Using the Spiral Process

Using the polymer, extruder and quench tank of Example 1, a Spiral web as depicted in FIG. 2 can also be made. A suitable die consists of a linear array of 25 inner orifices (0.019 inch diameter), each of which is surrounded by a ring (0.080 inch diameter) of 8 equally spaced outer orifices (0.010 inch diameter). The resulting web is vertically collected between 2 pairs of nip rollers in a quench tank which contains cold water. The web should be about 0.065 inches thick, although adjustment to the nip roller gap can change the web thickness.

Example 12

Casting Article Produced Using the Nomad Process

Figure 3A:
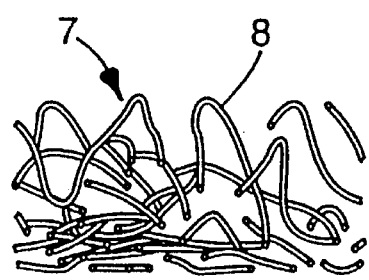
FIG. 3A is an enlarged detail view illustrating the three dimensional arrangement of filaments in a narrow segment of a typical web as made by the "Nomad™" process depicted (hereinafter referred to as the Nomad process) in U.S. Pat. No. 4,351,683.
Figure 3B:
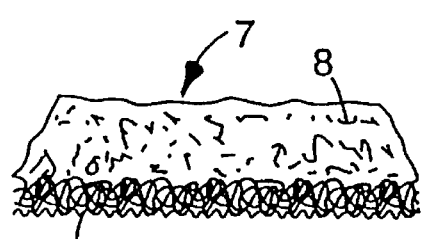
FIG. 3B is a representation in perspective of a segment of a web as made by the Nomad process.
Figure 4:
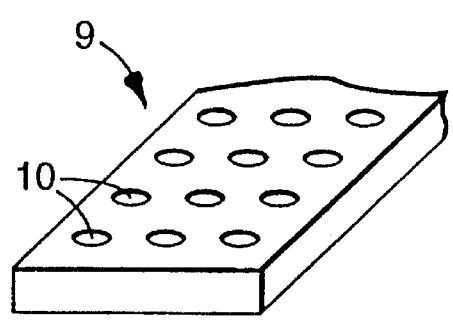
FIG. 4 depicts an extruded sheet comprising a plurality of apertures which have been formed by a secondary operation.

Using the polymer, extruder and quench tank of Example 1, a random web as depicted in FIGS. 3a and 3b can also be made. A suitable die consists of 3 rows of orifices, each row being spaced 0.100 inches apart, with individual orifices spaced 0.060 inches apart and having a 0.017 inch diameter. The extruded filaments are allowed to fall on the surface of one of the nip rollers to create a flattened surface. The web thickness and aperture volume is controlled by the spacing of the nip rollers and the take up speed of the rollers relative to the extrudate flow rate.

What is claimed is:

1. A method of enclosing a body member, comprising the steps of:

heating an apertured, extruded sheet, said sheet having a plurality of extruded filaments of a low temperature thermoplastic polymer having a softening or melting temperature less than about 90° C.;

wrapping the article about the body member; and molding the wrapped article about the body member such that the article is used as an orthopedic casting material and has a sufficient number of apertures after application to the patient to allow moisture vapors produced by the skin to freely escape through the casting material.

2. A method according to claim 1, wherein said extruded filaments comprise a filament-forming extrudable plastic mass having a tacky first state which permits said filaments to bond to one another at points of mutual contact and a second physical state in which said filaments have sufficient structural integrity to maintain their extruded bonded shape; wherein at least a portion of said filaments undulate thereby causing contact between said filaments while said filaments are sufficiently tacky to cause bonding therebetween at points of contact; and wherein said plastic mass changes from said tacky first state to said second physical state.

3. A method according to claim 2, wherein said low temperature thermoplastic polymer is selected from the group consisting of polyurethane, polyethylene, ethylene vinyl acetate, polyisoprene, and polyester.

4. A method according to claim 3, wherein said sheet has at least 20 percent aperture volume.

5. A method according to claim 3, wherein said sheet further comprises an inorganic or organic filler and said sheet has a yield stress of at least 500 dyne/cm² when heated to a temperature at which said sheet is wrapped about said body member.

6. A method according to claim 3, wherein said sheet further comprises a higher melting temperature secondary polymer and said sheet has a yield stress of at least 500 dyne/cm$^2$ when heated to a temperature at which said sheet is wrapped about said body member.

7. A method of enclosing a body member, comprising the steps of:

initiating the cure of an apertured, extruded sheet, said sheet comprising a viscous curable resin having a sufficient yield stress to resist flow at 25° C. for extended periods of time;

wrapping the article about the body member; and molding the wrapped article about the body member such that the article is used as an orthopedic casting material and has a sufficient number of apertures after application to the body member to allow moisture vapors produced by the skin to freely escape through the orthopedic casting material.

8. A method according to claim 7, wherein said apertured, extruded sheet comprises a plurality of straight spaced parallel elements of a first filament-forming extrudable plastic mass and a plurality of second elements of a second filament-forming extrudable plastic mass having a cross-section with an aspect ratio of at least two; wherein said plastic masses have a tacky first state which permits said elements to bond to one another at points of mutual contact and a second physical state in which said elements have sufficient structural integrity to maintain their extruded bonded shape: wherein said second elements undulate thereby causing contact and bonding between said first and second elements; wherein said plastic masses change from said tacky first state to said second physical state; wherein said sheet has between 7.75 and 77.50 apertures per cm$^2$ and a tensile strength, prior to being cured, of at least 0.0875 N/mm width; and wherein said viscous curable resin is water-curable and is selected from the group consisting of isocyanate functional prepolymers, liquid organometallic compounds, and water curable alkoxy silane terminated oligomers.

9. A method according to claim 7, wherein said apertured, extruded sheet comprises a plurality of elements of a filament-forming extrudable plastic mass comprising one or more inner filaments and a plurality of outer filaments; wherein said plastic mass has a tacky first state which permits said filaments to bond to one another at points of mutual contact and a second physical state in which said filaments have sufficient structural integrity to maintain their extruded bonded shape; wherein said inner filaments undulate thereby causing contact and bonding between said inner and outer elements; wherein said plastic masses change from said tacky first state to said second physical state; wherein said sheet has at least 20 percent aperture volume and a tensile strength, prior to being cured, of at least 0.0875 N/mm width; and wherein said viscous curable resin is water-curable and is selected from the group consisting of isocyanate functional prepolymers, liquid organometallic compounds, and water curable alkoxy silane terminated oligomers.

10. A method according to claim 7, wherein said apertured, extruded sheet comprises a web of elements of a filament-forming extrudable plastic mass; wherein said plastic mass has a tacky first state which permits said elements to bond to one another at points of mutual contact and a second physical state in which said elements have sufficient structural integrity to maintain their extruded bonded shape; wherein said elements undulate thereby causing contact and bonding between said elements; wherein said plastic masses change from said tacky first state to said second physical state; wherein said sheet has at least 20 percent aperture volume and a tensile strength, prior to being cured, of at least 0.0875 N/mm width; and wherein said viscous curable resin is water-curable and is selected from the group consisting of isocyanate functional prepolymers, liquid organometallic compounds, and water curable alkoxy silane terminated oligomers.

11. A method according to claim 7, wherein said viscous curable resin comprises a sufficient amount of a high molecular weight secondary polymer such that the mixture of said resin and said secondary polymer has a tan δ less than 20 at 1.0 rad/sec.

12. A method according to claim 7, wherein said viscous curable resin further comprises a sufficient amount of a second reactive monomer or oligomer such that when said second reactive monomer or oligomer has been polymerized the mixture of said resin and said polymerized second reactive monomer or oligomer has a tan delta less than 10 at 1.0 rad/sec.

13. A method of enclosing a body member, comprising the steps of:

heating an apertured, extruded sheet, wherein said extruded sheet comprises a low temperature thermoplastic polymer having a softening or melting temperature less than about 90° C. and a plurality of apertures through the extruded sheet;

wrapping the heated sheet about the body member; and molding the wrapped sheet about the body member such that the sheet is used as an orthopedic casting material and has a sufficient number of apertures after application to the patient to allow moisture vapors produced by the skin to freely escape through the orthopedic casting material.

14. A method of enclosing a body member according to claim 13, wherein said thermoplastic polymer comprises polycaprolactone and said sheet comprises from 1.55 to 46.5 apertures per square cm.

15. A method of enclosing a body member according to claim 14, wherein said sheet is in the form of an orthopedic casting material which when wrapped about the body member comprises a plurality of layers which adhere well to each other.

16. A method of enclosing a body member according to claim 1, wherein said thermoplastic polymer comprises polycaprolactone.

17. A method of enclosing a body member according to claim 1, wherein said article is in the form of an orthopedic casting material which when wrapped about the body member comprises a plurality of layers which adhere well to each other.

* * * * *

UNITED STATES PATENT AND TRADEMARK OFFICE
CERTIFICATE OF CORRECTION

PATENT NO.: 5,584,800
DATED: December 17, 1996
INVENTOR(S): Matthew T. Scholz, Jason L. Edgar and Dennis G. Welygan It is certified that error appears in the above-identified patent and that said Letters Patent is hereby corrected as shown below:

Col. 1, line 19, "Pads" should read -- Paris --.

Col. 1, line 26, "Pads" should read -- Paris --.

Col. 1, line 28, "Pads" should read -- Paris --.

Col. 1, line 36, "an" should read -- art --.

Col. 5, line 7, "east" should read -- cast --.

Col. 7, line 46, "theology" should read -- rheology --.

Col. 10, line 13, "kerimine" should read -- ketimine --.

Col. 16, line 52, "an" should read -- art --.

Col. 19, line 15, "rosin" should read -- resin --.

Col. 19, line 64, "bending" should read -- bonding --.

Col. 26, line 14, "Coming" should read -- Corning --.

Col. 27, line 19, "Coming" should read -- Corning --.

Signed and Sealed this

Sixteenth Day of June, 1998

*Attest:*

BRUCE LEHMAN

*Attesting Officer*         *Commissioner of Patents and Trademarks*